(12) United States Patent
Dryga et al.

(10) Patent No.: US 9,863,940 B2
(45) Date of Patent: Jan. 9, 2018

(54) METHODS FOR ISOLATING A TARGET ANALYTE FROM A HETEROGENOUS SAMPLE

(71) Applicant: DNAE Group Holdings Limited, London (GB)

(72) Inventors: Sergey A. Dryga, Albuquerque, NM (US); Victor C. Esch, Albuquerque, NM (US); Lisa-Jo Ann Clarizia, Albuquerque, NM (US); Eddie W. Adams, Albuquerque, NM (US); Thearith H. Ung, Albuquerque, NM (US); Ravil A. Sitdikov, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 0 days.

(21) Appl. No.: 15/607,983

(22) Filed: May 30, 2017

(65) Prior Publication Data

US 2017/0261501 A1  Sep. 14, 2017

Related U.S. Application Data

(63) Continuation of application No. 14/478,692, filed on Sep. 5, 2014, now Pat. No. 9,696,302, which is a continuation of application No. 13/091,510, filed on Apr. 21, 2011, now Pat. No. 8,841,104.

(60) Provisional application No. 61/326,588, filed on Apr. 21, 2010.

(51) Int. Cl.
| | | |
|---|---|---|
| *C12Q 1/00* | (2006.01) |
| *G01N 33/543* | (2006.01) |
| *B01L 3/00* | (2006.01) |
| *G01N 21/64* | (2006.01) |
| *G01N 33/53* | (2006.01) |
| *C12Q 1/68* | (2006.01) |

(52) U.S. Cl.
CPC .... *G01N 33/5434* (2013.01); *B01L 3/502738* (2013.01); *G01N 21/64* (2013.01); *G01N 33/53* (2013.01); *B01L 2300/0636* (2013.01); *C12Q 1/68* (2013.01); *G01N 2446/90* (2013.01)

(58) Field of Classification Search
CPC . C12M 1/34; C12M 3/00; F16K 17/00; C08F 12/20; G01F 1/66; G01F 15/00; G05D 7/01
USPC ......................................... 435/4, 7.1, 34, 39
See application file for complete search history.

(56) References Cited

U.S. PATENT DOCUMENTS

2008/0241909 A1* 10/2008 Jung ................ G01N 33/54326
435/287.1

* cited by examiner

*Primary Examiner* — Jana A Hines
(74) *Attorney, Agent, or Firm* — Brown Rudnick LLP; Thomas C. Meyers

(57) ABSTRACT

The invention generally relates to methods of using compositions that include sets of magnetic particles, members of each set being conjugated to an antibody specific for a pathogen, and magnets to isolate a pathogen from a body fluid sample.

19 Claims, No Drawings

METHODS FOR ISOLATING A TARGET ANALYTE FROM A HETEROGENOUS SAMPLE

RELATED APPLICATION

The present application is a continuation of U.S. non-provisional application Ser. No. 14/487,692, filed Sep. 5, 2014, which is a continuation of U.S. non-provisional application Ser. No. 13/091,510, filed Apr. 21, 2011, which claims the benefit of and priority to U.S. provisional patent application Ser. No. 61/326,588, filed Apr. 21, 2010, the contents of each of which are incorporated by reference herein in their entirety.

FIELD OF THE INVENTION

The invention generally relates to methods of using compositions that include sets of magnetic particles, members of each set being conjugated to an antibody specific for a pathogen, and magnets to isolate a pathogen from a body fluid sample.

BACKGROUND

Blood-borne pathogens are a significant healthcare problem. A delayed or improper diagnosis of a bacterial infection can result in sepsis, a serious, and often deadly, inflammatory response to the infection. Sepsis is the $10^{th}$ leading cause of death in the United States. Early detection of bacterial infections in blood is the key to preventing the onset of sepsis. Traditional methods of detection and identification of blood-borne infection include blood culture and antibiotic susceptibility assays. Those methods typically require culturing cells, which can be expensive and can take as long as 72 hours. Often, septic shock will occur before cell culture results can be obtained.

Alternative methods for detection of pathogens, particularly bacteria, have been described by others. Those methods include molecular detection methods, antigen detection methods, and metabolite detection methods. Molecular detection methods, whether involving hybrid capture or polymerase chain reaction (PCR), require high concentrations of purified DNA for detection. Both antigen detection and metabolite detection methods also require a relatively large amount of bacteria and have high limit of detection (usually $>10^4$ CFU/mL), thus requiring an enrichment step prior to detection. This incubation/enrichment period is intended to allow for the growth of bacteria and an increase in bacterial cell numbers to more readily aid in identification. In many cases, a series of two or three separate incubations is needed to isolate the target bacteria. However, such enrichment steps require a significant amount of time (e.g., at least a few days to a week) and can potentially compromise test sensitivity by killing some of the cells sought to be measured.

There is a need for methods for isolating target analytes, such as bacteria, from a sample, such as a blood sample, without an additional enrichment step. There is also a need for methods of isolating target analytes that are fast and sensitive in order to provide data for patient treatment decisions in a clinically relevant time frame.

SUMMARY

The present invention provides methods for isolating pathogens in a biological sample. The invention allows the rapid detection of pathogen at very low levels in the sample; thus enabling early and accurate detection and identification of the pathogen. The invention is carried out using sets of magnetic particles, members of each set being conjugated to a binding element, such as an antibody, that is specific for a pathogen. The invention allows detection of pathogen in a heterogeneous biological sample at levels of from about 10 CFU/ml to about 1 CFU/ml.

Methods of the invention involve introducing magnetic particles to a biological sample (e.g., a tissue or body fluid sample). The sample is incubated to allow the particles to bind to pathogen in the sample, and a magnetic field is applied to capture pathogen/magnetic particle complexes on a surface. Optionally, the surface can be washed with a wash solution that reduces particle aggregation, thereby isolating pathogen/magnetic particle complexes. A particular advantage of compositions of the invention is for capture and isolation of bacteria and fungi directly from blood samples at low concentrations that are present in many clinical samples (as low as 1 CFU/ml of bacteria in a blood sample). Preferably, the magnetic particles comprise a pathogen binding element that has one or more magnetic particles attached to it.

In certain aspects, methods of the invention involve obtaining a heterogeneous sample including a pathogen, exposing the sample to a cocktail including a plurality of sets of magnetic particles, members of each set being conjugated to an antibody specific for a pathogen, and separating particle bound pathogen from other components in the sample. Methods of the invention may further involve characterizing the pathogen. Characterizing may include identifying the pathogen by any technique known in the art. Exemplary techniques include sequencing nucleic acid derived from the pathogen or amplifying the nucleic acid.

The antibodies conjugated to the particles may be either monoclonal or polyclonal antibodies. Methods of the invention may be used to isolate pathogen from heterogeneous sample. In particular embodiments, the heterogeneous sample is a blood sample.

Since each set of particles is conjugated with antibodies have different specificities for different pathogens, compositions of the invention may be provided such that each set of antibody conjugated particles is present at a concentration designed for detection of a specific pathogen in the sample. In certain embodiments, all of the sets are provided at the same concentration. Alternatively, the sets are provided at different concentrations.

To facilitate detection of the different sets of pathogen/magnetic particle complexes the particles may be differently labeled. Any detectable label may be used with compositions of the invention, such as fluorescent labels, radiolabels, enzymatic labels, and others. In particular embodiments, the detectable label is an optically-detectable label, such as a fluorescent label. Exemplary fluorescent labels include Cy3, Cy5, Atto, cyanine, rhodamine, fluorescien, coumarin, BODIPY, alexa, and conjugated multi-dyes.

Methods of the invention may be used to isolate only gram positive bacteria from a sample. Alternatively, methods of the invention may be used to isolate only gram negative bacteria from a sample. In certain embodiments, methods of the invention are used to isolate both gram positive and gram negative bacteria from a sample. In still other embodiments, methods isolate specific pathogen from a sample. Exemplary bacterial species that may be captured and isolated by methods of the invention include *E. coli*, *Listeria*, *Clostridium*, *Mycobacterium*, *Shigella*, *Borrelia*,

*Campylobacter, Bacillus, Salmonella, Staphylococcus, Enterococcus, Pneumococcus, Streptococcus*, and a combination thereof.

Methods of the invention are not limited to isolating pathogens from a body fluid. Methods of the invention may be designed to isolate other types of target analytes, such as fungi, protein, a cell, a virus, a nucleic acid, a receptor, a ligand, or any molecule known in the art.

Compositions used in methods of the invention may use any type of magnetic particle. Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In other embodiments, the magnetic particles include at least 70% superparamagnetic particles by weight. In certain embodiments, the superparamagnetic particles are from about 100 nm to about 250 nm in diameter. In certain embodiments, the magnetic particle is an iron-containing magnetic particle. In other embodiments, the magnetic particle includes iron oxide or iron platinum.

Another aspect of the invention provides methods for isolating pathogen from a heterogeneous sample, that involve labeling pathogen from a biological sample with a cocktail including a plurality of sets of magnetic particles, members of each set being conjugated to an antibody specific for a pathogen, exposing the sample to a magnetic field to isolate pathogen conjugated to the particles, and isolating particle bound pathogen from other components of the sample. Methods of the invention may further involve eluting pathogen from the particles. Methods of the invention may further involve characterizing the pathogen. Characterizing may include identifying the pathogen by any technique known in the art. Exemplary techniques include sequencing nucleic acid derived from the pathogen or amplifying the nucleic acid.

DETAILED DESCRIPTION

The invention generally relates to methods of using compositions that include sets of magnetic particles, members of each set being conjugated to an antibody specific for a pathogen, and magnets to isolate a pathogen from a body fluid sample. Certain fundamental technologies and principles are associated with binding magnetic materials to target entities and subsequently separating by use of magnet fields and gradients. Such fundamental technologies and principles are known in the art and have been previously described, such as those described in Janeway (Immunobiology, 6$^{th}$ edition, Garland Science Publishing), the content of which is incorporated by reference herein in its entirety.

Composition used in methods of the invention may use any type of magnetic particle. Production of magnetic particles and particles for use with the invention are known in the art. See for example Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In certain embodiments, the magnetic particle is an iron containing magnetic particle. In other embodiments, the magnetic particle includes iron oxide or iron platinum.

In certain embodiments, the magnetic particles include at least about 10% superparamagnetic particles by weight, at least about 20% superparamagnetic particles by weight, at least about 30% superparamagnetic particles by weight, at least about 40% superparamagnetic particles by weight, at least about 50% superparamagnetic particles by weight, at least about 60% superparamagnetic particles by weight, at least about 70% superparamagnetic particles by weight, at least about 80% superparamagnetic particles by weight, at least about 90% superparamagnetic particles by weight, at least about 95% superparamagnetic particles by weight, or at least about 99% superparamagnetic particles by weight. In a particular embodiment, the magnetic particles include at least about 70% superparamagnetic particles by weight.

In certain embodiments, the superparamagnetic particles are less than 100 nm in diameter. In other embodiments, the superparamagnetic particles are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic particles are from about 100 nm to about 250 nm in diameter.

In certain embodiments, the particles are particles (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue particle aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the particles. It may also be advantageous to have the volumetric loading in a particle be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3T.

The size of the nanometal containing particle may be optimized for a particular application, for example, maximizing moment loaded upon a target, maximizing the number of particles on a target with an acceptable detectability, maximizing desired force-induced motion, and/or maximizing the difference in attached moment between the labeled target and non-specifically bound targets or particle aggregates or individual particles. While maximizing is referenced by example above, other optimizations or alterations are contemplated, such as minimizing or otherwise desirably affecting conditions.

In an exemplary embodiment, a polymer particle containing 80 wt % $Fe_3O_4$ superparamagnetic particles, or for example, 90 wt % or higher superparamagnetic particles, is produced by encapsulating superparamagnetic particles with a polymer coating to produce a particle having a diameter of about 250 nm.

Each set of magnetic particles has a target-specific binding moiety that allows for each set to specifically bind the target of interest in the heterogeneous sample. The target-specific moiety may be any molecule known in the art and will depend on the target to be captured and isolated. Exemplary target-specific binding moieties include nucleic acids, proteins, ligands, antibodies, aptamers, and receptors.

In particular embodiments, the target-specific binding moiety is an antibody, such as an antibody that binds a particular bacterium. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such as the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic particles against *Salmonella* are provided in Vermunt et al. (J. Appl. Bact. 72:112, 1992). Immunomagnetic particles against *Staphylococcus aureus* are provided in Johne et al. (J. Clin. Microbiol. 27:1631, 1989). Immunomagnetic particles against *Listeria* are provided in Skjerve et al. (Appl. Env. Microbiol. 56:3478, 1990). Immunomagnetic particles against *Escherichia coli* are provided in Lund et al. (J. Clin. Microbiol. 29:2259, 1991).

Methods for attaching the target-specific binding moiety to the magnetic particle are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

Since each set of particles is conjugated with antibodies having different specificities for different pathogens, compositions used in methods of the invention may be provided such that each set of antibody conjugated particles is present at a concentration designed for detection of a specific pathogen in the sample. In certain embodiments, all of the sets are provided at the same concentration. Alternatively, the sets are provided at different concentrations. For example, compositions may be designed such that sets that bind gram positive bacteria are added to the sample at a concentration of $2 \times 10^9$ particles per/ml, while sets that bind gram negative bacteria are added to the sample at a concentration of $4 \times 10^9$ particles per/ml. Compositions used with methods of the invention are not affected by antibody cross-reactivity. However, in certain embodiments, sets are specifically designed such that there is no cross-reactivity between different antibodies and different sets.

Methods of the invention may be used to isolate only gram positive bacteria from a sample. Alternatively, methods of the invention may be used to isolate only gram negative bacteria from a sample. In certain embodiments, methods of the invention are used to isolate both gram positive and gram negative bacteria from a sample. Such compositions allow for isolation of essentially all bacteria from a sample.

In still other embodiments, compositions used with methods of the invention are designed to isolate specific pathogen from a sample. Exemplary bacterial species that may be captured and isolated by methods of the invention include *E. coli, Listeria, Clostridium, Mycobacterium, Shigella, Borrelia, Campylobacter, Bacillus, Salmonella, Staphylococcus, Enterococcus, Pneumococcus, Streptococcus*, and a combination thereof. These sets can be mixed together to isolate for example, *E. coli* and *Listeria*; or *E. coli, Listeria, and Clostridium*; or *Mycobacterium, Campylobacter, Bacillus, Salmonella*, and *Staphylococcus*, etc. Any combination of sets may be used and compositions of the invention will vary depending on the suspected pathogen or pathogens to be isolated.

Capture of a wide range of target microorganisms simultaneously can be achieved by utilizing antibodies specific to target class, such as pan-Gram-positive antibodies, pan-Gran-negative antibodies or antibodies specific to a subset of organisms of a certain class. Further, expanded reactivity can be achieved by mixing particles of different reactivity. It was shown in our experiments that addition of high concentration of non-specific particles does not interfere with the capture efficiency of target-specific particles. Similarly, several different particle preparations can be combined to allow for the efficient capture of desired pathogens. In certain embodiments the particles can be utilized at a concentration between $1 \times 10^8$ and $5 \times 10^{10}$ particles/mL.

In certain embodiments the expanded coverage can be provided by mixing antibodies with different specificity before attaching them to magnetic particles. Purified antibodies can be mixed and conjugated to activated magnetic particle using standard methods known in the art.

To facilitate detection of the different sets of pathogen/magnetic particle complexes the particles may be differently labeled. Any detectable label may be used with compositions of the invention, such as fluorescent labels, radiolabels, enzymatic labels, and others. The detectable label may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoulaurin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels. Methods of linking fluorescent labels to magnetic particles or antibodies are known in the art.

Methods of the invention may be used to isolate pathogen from any heterogeneous sample. In particular embodiments, methods of the invention isolate a pathogen from body fluid. A body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material.

In particular embodiments, the fluid is blood. Methods of the invention allow for bacteria in a blood sample to be isolated and detected at a level as low as or even lower than 1 CFU/ml. Blood may be collected in a container, such as a blood collection tube (e.g., VACUTAINER, test tube specifically designed for venipuncture, commercially available from Becton, Dickinson and company). In certain embodiments, a solution is added that prevents or reduces aggregation of endogenous aggregating factors, such as heparin in the case of blood.

The blood sample is then mixed with compositions as described above to generate a mixture that is allowed to incubate such that the compositions bind to at least one bacterium in the blood sample. The type or types of bacteria that will bind compositions of the invention will depend on the design of the composition, i.e., which antibody conjugated particles are used. The mixture is allowed to incubate for a sufficient time to allow for the composition to bind to the pathogen in the blood. The process of binding the composition to the pathogen associates a magnetic moment with the pathogen, and thus allows the pathogen to be manipulated through forces generated by magnetic fields upon the attached magnetic moment.

In general, incubation time will depend on the desired degree of binding between the pathogen and the compositions of the invention (e.g., the amount of moment that would be desirably attached to the pathogen), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

In certain embodiments, a buffer solution is added to the sample along with the compositions of the invention. An exemplary buffer includes Tris(hydroximethyl)-aminomethane hydrochloride at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in methods of the invention are designed to prevent lysis of blood cells, facilitate efficient binding of targets with magnetic particles and to reduce formation of particle aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic particle through ionic interaction. Tris(hydroxymethyl)-aminomethane hydrochloride is a well established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

Additional compounds can be used to modulate the capture efficiency by blocking or reducing non-specific interaction with blood components and either magnetic particles or pathogens. For example, chelating compounds, such as EDTA or EGTA, can be used to prevent or minimize interactions that are sensitive to the presence of $Ca^{2+}$ or $Mg^{2+}$ ions.

An alternative approach to achieve high binding efficiency while reducing time required for the binding step is to use static mixer, or other mixing devices that provide efficient mixing of viscous samples at high flow rates, such as at or around 5 mL/min. In one embodiment, the sample is mixed with binding buffer in ratio of, or about, 1:1, using a mixing interface connector. The diluted sample then flows through a mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing.

After binding of the compositions to the pathogen in the sample to form pathogen/magnetic particle complexes, a magnetic field is applied to the mixture to capture the complexes on a surface. Components of the mixture that are not bound to magnetic particles will not be affected by the magnetic field and will remain free in the mixture. Methods and apparatuses for separating target/magnetic particle complexes from other components of a mixture are known in the art. For example, a steel mesh may be coupled to a magnet, a linear channel or channels may be configured with adjacent magnets, or quadrapole magnets with annular flow may be used. Other methods and apparatuses for separating target/magnetic particle complexes from other components of a mixture are shown in Rao et al. (U.S. Pat. No. 6,551,843), Liberti et al. (U.S. Pat. No. 5,622,831), Hatch et al. (U.S. Pat. No. 6,514,415), Benjamin et al. (U.S. Pat. No. 5,695,946), Liberti et al. (U.S. Pat. No. 5,186,827), Wang et al. (U.S. Pat. No. 5,541,072), Liberti et al. (U.S. Pat. No. 5,466,574), and Terstappen et al. (U.S. Pat. No. 6,623,983), the content of each of which is incorporated by reference herein in its entirety.

In certain embodiments, the magnetic capture is achieved at high efficiency by utilizing a flow-through capture cell with a number of strong rare earth bar magnets placed perpendicular to the flow of the sample. When using a flow chamber with flow path cross-section 0.5 mm×20 mm (h×w) and 7 bar NdFeB magnets, the flow rate could be as high as 5 mL/min or more, while achieving capture efficiency close to 100%.

The above described type of magnetic separation produces efficient capture of a target analyte and the removal of a majority of the remaining components of a sample mixture. However, such a process produces a sample that contains a very high percent of magnetic particles that are not bound to target analytes because the magnetic particles are typically added in excess, as well as non-specific target entities. Non-specific target entities may for example be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

For example, in the case of immunomagnetic binding of bacteria or fungi in a blood sample, the sample may include: bound targets at a concentration of about 1/mL or a concentration less than about $10^6$/mL; background particles at a concentration of about $10^7$/ml to about $10^{10}$/ml; and non-specific targets at a concentration of about 10/ml to about $10^5$/ml.

The presence of magnetic particles that are not bound to target analytes and non-specific target entities on the surface that includes the target/magnetic particle complexes interferes with the ability to successfully detect the target of interest. The magnetic capture of the resulting mix, and close contact of magnetic particles with each other and bound targets, result in the formation of aggregate that is hard to dispense and which might be resistant or inadequate for subsequent processing or analysis steps. In order to remove magnetic particles that are not bound to target analytes and non-specific target entities, the surface may be washed with a wash solution that reduces particle aggregation, thereby isolating target/magnetic particle complexes from the magnetic particles that are not bound to target analytes and non-specific target entities. The wash solution minimizes the formation of the aggregates.

Any wash solution that imparts a net negative charge to the magnetic particle that is not sufficient to disrupt interaction between the target-specific moiety of the magnetic particle and the target analyte may be used. Without being limited by any particular theory or mechanism of action, it is believed that attachment of the negatively charged molecules in the wash solution to magnetic particles provides net negative charge to the particles and facilitates dispersal of non-specifically aggregated particles. At the same time, the net negative charge is not sufficient to disrupt strong interaction between the target-specific moiety of the magnetic particle and the target analyte (e.g., an antibody-antigen interaction). Exemplary solutions include heparin, Tris-HCl, Tris-borate-EDTA (TBE), Tris-acetate-EDTA (TAE), Tris-cacodylate, HEPES (4-(2-hydroxyethyl)-1-piperazineethanesulphonic acid), PBS (phosphate buffered saline), PIPES (piperazine-N,N'-bis(2-ethanesulfonic acid), MES (2-N-morpholino)ethanesulfonic acid), Tricine (N-(Tri (hydroximethyl)methyl)glycine), and similar buffering agents. In certain embodiments, only a single wash cycle is performed. In other embodiments, more than one wash cycle is performed.

In particular embodiments, the wash solution includes heparin. For embodiments in which the body fluid sample is blood, the heparin also reduces probability of clotting of blood components after magnetic capture. The bound targets are washed with heparin-containing buffer 1-3 times to remove blood components and to reduce formation of aggregates.

Once the target/magnetic particle complexes are isolated, the target may be analyzed by a multitude of existing technologies, such as miniature NMR, Polymerase Chain Reaction (PCR), mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components. In one embodiment, isolated bacteria are eluted from the magnetic particles and are lysed with a chaotropic solution, and DNA is bound to DNA extraction resin. After washing of the resin, the bacterial DNA is eluted and used in quantitative RT-PCR to detect the presence of a specific species, and/or, subclasses of bacteria.

In another embodiment, captured bacteria is removed from the magnetic particles to which they are bound and the processed sample is mixed with fluorescent labeled antibodies specific to the bacteria or fluorescent Gram stain. After incubation, the reaction mixture is filtered through 0.2 μm to 1.0 μm filter to capture labeled bacteria while allowing majority of free particles and fluorescent labels to pass through the filter. Bacteria is visualized on the filter using microscopic techniques, e.g. direct microscopic observation, laser scanning or other automated methods of image capture. The presence of bacteria is detected through image analysis. After the positive detection by visual techniques, the bacteria can be further characterized using PCR or genomic methods.

Detection of bacteria of interest can be performed by use of nucleic acid probes following procedures which are known in the art. Suitable procedures for detection of bacteria using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/ reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Such protocols may be applied directly to the bacteria captured on the magnetic particles. The bacteria is combined with a lysis buffer and collected nucleic acid target molecules are then utilized as the template for the PCR reaction.

For detection of the selected bacteria by use of antibodies, isolated bacteria are contacted with antibodies specific to the bacteria of interest. As noted above, either polyclonal or monoclonal antibodies can be utilized, but in either case have affinity for the particular bacteria to be detected. These antibodies, will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

Detection of bacteria of interest using NMR may be accomplished as follows. In the use of NMR as a detection methodology, in which a sample is delivered to a detector coil centered in a magnet, the target of interest, such as a magnetically labeled bacterium, may be delivered by a fluid medium, such as a fluid substantially composed of water. In such a case, the magnetically labeled target may go from a region of very low magnetic field to a region of high magnetic field, for example, a field produced by an about 1 to about 2 Tesla magnet. In this manner, the sample may traverse a magnetic gradient, on the way into the magnet and on the way out of the magnet. As may be seen via equations 1 and 2 below, the target may experience a force pulling into the magnet in the direction of sample flow on the way into the magnet, and a force into the magnet in the opposite direction of flow on the way out of the magnet. The target may experience a retaining force trapping the target in the magnet if flow is not sufficient to overcome the gradient force.

$$m \text{ dot (del } B) = F \qquad \text{Equation 1}$$

$$v_t = -F/(6 * p * n * r) \qquad \text{Equation 2}$$

where n is the viscosity, r is the particle diameter, F is the vector force, B is the vector field, and m is the vector moment of the particle Magnetic fields on a path into a magnet may be non-uniform in the transverse direction with respect to the flow into the magnet. As such, there may be a transverse force that pulls targets to the side of a container or a conduit that provides the sample flow into the magnet. Generally, the time it takes a target to reach the wall of a conduit is associated with the terminal velocity and is lower with increasing viscosity. The terminal velocity is associated with the drag force, which may be indicative of creep flow in certain cases. In general, it may be advantageous to have a high viscosity to provide a higher drag force such that a target will tend to be carried with the fluid flow through the magnet without being trapped in the magnet or against the conduit walls.

Newtonian fluids have a flow characteristic in a conduit, such as a round pipe, for example, that is parabolic, such that the flow velocity is zero at the wall, and maximal at the center, and having a parabolic characteristic with radius. The velocity decreases in a direction toward the walls, and it is easier to magnetically trap targets near the walls, either with transverse gradients force on the target toward the conduit wall, or in longitudinal gradients sufficient to prevent target flow in the pipe at any position. In order to provide favorable fluid drag force to keep the samples from being trapped in the conduit, it may be advantageous to have a plug flow condition, wherein the fluid velocity is substantially uniform as a function of radial position in the conduit.

When NMR detection is employed in connection with a flowing sample, the detection may be based on a perturbation of the NMR water signal caused by a magnetically labeled target (Sillerud et al., JMR (Journal of Magnetic Resonance), vol. 181, 2006). In such a case, the sample may be excited at time 0, and after some delay, such as about 50 ms or about 100 ms, an acceptable measurement (based on a detected NMR signal) may be produced. Alternatively, such a measurement may be produced immediately after excitation, with the detection continuing for some duration, such as about 50 ms or about 100 ms. It may be advantageous to detect the NMR signal for substantially longer time durations after the excitation.

By way of example, the detection of the NMR signal may continue for a period of about 2 seconds in order to record spectral information at high-resolution. In the case of parabolic or Newtonian flow, the perturbation excited at time 0 is typically smeared because the water around the perturbation source travels at different velocity, depending on radial position in the conduit. In addition, spectral information may be lost due to the smearing or mixing effects of the differential motion of the sample fluid during signal detection. When carrying out an NMR detection application involving a flowing fluid sample, it may be advantageous to provide plug-like sample flow to facilitate desirable NMR contrast and/or desirable NMR signal detection.

Differential motion within a flowing Newtonian fluid may have deleterious effects in certain situations, such as a situation in which spatially localized NMR detection is desired, as in magnetic resonance imaging. In one example, a magnetic object, such as a magnetically labeled bacterium, is flowed through the NMR detector and its presence and location are detected using MRI techniques. The detection may be possible due to the magnetic field of the magnetic object, since this field perturbs the magnetic field of the fluid in the vicinity of the magnetic object. The detection of the magnetic object is improved if the fluid near the object remains near the object. Under these conditions, the magnetic perturbation may be allowed to act longer on any given volume element of the fluid, and the volume elements of the fluid so affected will remain in close spatial proximity. Such a stronger, more localized magnetic perturbation will be more readily detected using NMR or MRI techniques.

If a Newtonian fluid is used to carry the magnetic objects through the detector, the velocity of the fluid volume elements will depend on radial position in the fluid conduit. In such a case, the fluid near a magnetic object will not remain near the magnetic object as the object flows through the detector. The effect of the magnetic perturbation of the object on the surrounding fluid may be smeared out in space, and the strength of the perturbation on any one fluid volume element may be reduced because that element does not stay within range of the perturbation. The weaker, less-well-localized perturbation in the sample fluid may be undetectable using NMR or MRI techniques.

Certain liquids, or mixtures of liquids, exhibit non-parabolic flow profiles in circular conduits. Such fluids may exhibit non-Newtonian flow profiles in other conduit shapes. The use of such a fluid may prove advantageous as the detection fluid in an application employing an NMR-based detection device. Any such advantageous effect may be attributable to high viscosity of the fluid, a plug-like flow profile associated with the fluid, and/or other characteristic(s) attributed to the fluid that facilitate detection. As an example, a shear-thinning fluid of high viscosity may exhibit a flow velocity profile that is substantially uniform across the central regions of the conduit cross-section. The velocity profile of such a fluid may transition to a zero or very low value near or at the walls of the conduit, and this transition region may be confined to a very thin layer near the wall.

Not all fluids, or all fluid mixtures, are compatible with the NMR detection methodology. In one example, a mixture of glycerol and water can provide high viscosity, but the NMR measurement is degraded because separate NMR signals are detected from the water and glycerol molecules making up the mixture. This can undermine the sensitivity of the NMR detector. In another example, the non-water component of the fluid mixture can be chosen to have no NMR signal, which may be achieved by using a perdeuterated fluid component, for example, or using a perfluorinated fluid component. This approach may suffer from the loss of signal intensity since a portion of the fluid in the detection coil does not produce a signal.

Another approach may be to use a secondary fluid component that constitutes only a small fraction of the total fluid mixture. Such a low-concentration secondary fluid component can produce an NMR signal that is of negligible intensity when compared to the signal from the main component of the fluid, which may be water. It may be advantageous to use a low-concentration secondary fluid component that does not produce an NMR signal in the detector. For example, a perfluorinated or perdeuterated secondary fluid component may be used. The fluid mixture used in the NMR detector may include one, two, or more than two secondary components in addition to the main fluid component. The fluid components employed may act in concert to produce the desired fluid flow characteristics, such as high-viscosity and/or plug flow. The fluid components may be useful for providing fluid characteristics that are advantageous for the performance of the NMR detector, for example by providing NMR relaxation times that allow faster operation or higher signal intensities.

A non-Newtonian fluid may provide additional advantages for the detection of objects by NMR or MRI techniques. As one example, the objects being detected may all have substantially the same velocity as they go through the detection coil. This characteristic velocity may allow simpler or more robust algorithms for the analysis of the detection data. As another example, the objects being detected may have fixed, known, and uniform velocity. This may prove advantageous in devices where the position of the detected object at later times is needed, such as in a device that has a sequestration chamber or secondary detection chamber down-stream from the NMR or MRI detection coil, for example.

In an exemplary embodiment, sample delivery into and out of a 1.7T cylindrical magnet using a fluid delivery medium containing 0.1% to 0.5% Xanthan gum in water was successfully achieved. Such delivery is suitable to provide substantially plug-like flow, high viscosity, such as from about 10 cP to about 3000 cP, and good NMR contrast in relation to water. Xanthan gum acts as a non-Newtonian fluid, having characteristics of a non-Newtonian fluid that are well know in the art, and does not compromise NMR signal characteristics desirable for good detection in a desirable mode of operation.

In certain embodiments, methods of the invention are useful for direct detection of bacteria from blood. Such a process is described here. Sample is collected in sodium heparin tube by venipuncture, acceptable sample volume is about 1 mL to 10 mL. Sample is diluted with binding buffer and superparamagnetic particles having target-specific binding moieties are added to the sample, followed by incubation on a shaking incubator at 37° C. for about 30 min to 120 min. Alternative mixing methods can also be used. In a particular embodiment, sample is pumped through a static mixer, such that reaction buffer and magnetic particles are added to the sample as the sample is pumped through the mixer. This process allows for efficient integration of all components into a single fluidic part, avoids moving parts and separate incubation vessels and reduces incubation time.

Capture of the labeled targets allows for the removal of blood components and reduction of sample volume from 30 mL to 5 mL. The capture is performed in a variety of magnet/flow configurations. In certain embodiments, methods include capture in a sample tube on a shaking platform or capture in a flow-through device at flow rate of 5 mL/min, resulting in total capture time of 6 min.

After capture, the sample is washed with wash buffer including heparin to remove blood components and free particles. The composition of the wash buffer is optimized to reduce aggregation of free particles, while maintaining the integrity of the particle/target complexes.

The detection method is based on a miniature NMR detector tuned to the magnetic resonance of water. When the sample is magnetically homogenous (no bound targets), the NMR signal from water is clearly detectable and strong. The presence of magnetic material in the detector coil disturbs the magnetic field, resulting in reduction in water signal. One of the primary benefits of this detection method is that there is no magnetic background in biological samples which significantly reduces the requirements for stringency of sample processing. In addition, since the detected signal is generated by water, there is a built-in signal amplification which allows for the detection of a single labeled bacterium.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Sample

Blood samples from healthy volunteers were spiked with clinically relevant concentrations of bacteria (1-10 CFU/mL) including both laboratory strains and clinical isolates of the bacterial species most frequently found in bloodstream infections.

Example 2

Antibody Preparation

In order to generate polyclonal, pan-Gram-positive bacteria-specific IgG, a goat was immunized by first administering bacterial antigens suspended in complete Freund's adjuvant intra lymph node, followed by subcutaneous injection of bacterial antigens in incomplete Freund's adjuvant in 2 week intervals. The antigens were prepared for antibody production by growing bacteria to exponential phase ($OD_{600}$=0.4-0.8). Following harvest of the bacteria by centrifugation, the bacteria was inactivated using formalin fixation in 4% formaldehyde for 4 hr at 37° C. After 3 washes of bacteria with PBS (15 min wash, centrifugation for 20 min at 4000 rpm) the antigen concentration was measured using BCA assay and the antigen was used at 1 mg/mL for immunization. In order to generate Gram-positive bacteria-specific IgG, several bacterial species were used for inoculation: *Staphylococcus aureus, Staphylococcus epidermidis, Enterococcus faecium* and *Enterococcus fecalis*.

The immune serum was purified using affinity chromatography on a protein G sepharose column (GE Healthcare), and reactivity was determined using ELISA. Antibodies cross-reacting with Gram-negative bacteria and fungi were removed by absorption of purified IgG with formalin-fixed Gram-negative bacteria and fungi. The formalin-fixed organisms were prepared similar to as described above and mixed with IgG. After incubation for 2 hrs at room temperature, the preparation was centrifuged to remove bacteria. Final antibody preparation was clarified by centrifugation and used for the preparation of antigen-specific magnetic particles.

Pan-Gram-negative IgG were generated in a similar fashion using inactivated *Enterobacter cloacae, Pseudomonas aeruginosa, Serratia marcescens* and other gram-negative bacteria as immunogens. The IgG fraction of serum was purified using protein-G affinity chromatography as described above.

Similarly, target specific antibodies were generated by inoculation of goats using formalin-fixed bacteria, immunization was performed with 2 or more closely related organisms.

Example 3

Preparation of Antigen-Specific Magnetic Particles

Superparamagnetic particles were synthesized by encapsulating iron oxide nanoparticles (5-15 nm diameter) in a latex core and labeling with goat IgG. Ferrofluid containing nanoparticles in organic solvent was precipitated with ethanol, nanoparticles were resuspended in aqueous solution of styrene and surfactant Hitenol BC-10, and emulsified using sonication. The mixture was allowed to equilibrate overnight with stirring and filtered through 1.2 and 0.45 μm filters to achieve uniform micelle size. Styrene, acrylic acid and divinylbenzene were added in carbonate buffer at pH 9.6. The polymerization was initiated in a mixture at 70° C. with the addition of $K_2S_2O_8$ and the reaction was allowed to complete overnight. The synthesized particles were washed 3 times with 0.1% SDS using magnetic capture, filtered through 1.2, 0.8, and 0.45 μm filters and used for antibody conjugation.

The production of particles resulted in a distribution of sizes that may be characterized by an average size and a standard deviation. In the case of labeling and extracting of bacteria from blood, the average size for optimal performance was found to be between 100 and 350 nm, for example between 200 nm to 250 nm.

The purified IgG were conjugated to prepared particles using standard EDC/sulfo-NHS chemistry. After conjugation, the particles were resuspended in 0.1% BSA which is used to block non-specific binding sites on the particle and to increase the stability of particle preparation.

Example 4

Labeling of Rare Cells Using Excess of Magnetic Nanoparticles

Bacteria, present in blood during blood-stream infection, were magnetically labeled using the superparamagnetic particles prepared in Example 3 above. The spiked samples as described in Example 1 were diluted 3-fold with a Tris-based binding buffer and target-specific particles, followed by incubation on a shaking platform at 37° C. for up to 2 hr. The optimal concentration of particles was determined by titration and was found to be in the range between $1\times10^8$ and $5\times10^{10}$ particle/mL. After incubation, the labeled targets were magnetically separated followed by a wash step designed to remove blood products. See example 5 below.

Example 5

Magnetic Capture of Bound Bacteria

Blood including the magnetically labeled target bacteria and excess free particles were injected into a flow-through capture cell with a number of strong rare earth bar magnets placed perpendicular to the flow of the sample. With using a flow chamber with flow path cross-section 0.5 mm×20 mm (h×w) and 7 bar NdFeB magnets, a flow rate as high as 5 mL/min was achieved. After flowing the mixture through the channel in the presence of the magnet, a wash solution including heparin was flowed through the channel. The bound targets were washed with heparin-containing buffer one time to remove blood components and to reduce formation of magnetic particle aggregates. In order to effectively wash bound targets, the magnet was removed and captured magnetic material was resuspended in wash buffer, followed by re-application of the magnetic field and capture of the magnetic material in the same flow-through capture cell.

Removal of the captured labeled targets was possible after moving magnets away from the capture chamber and eluting with flow of buffer solution.

What is claimed is:

1. A method for isolating pathogen from a heterogeneous sample, the method comprising:
    providing a vessel that contains a heterogeneous sample comprising pathogen, the vessel being coupled to a fluidic device that comprises a channel and a magnet;
    introducing to the sample in the vessel a cocktail comprising a plurality of magnetic particles, conjugated to target-specific binding moieties that bind said pathogen, thereby forming a mixture comprising pathogen/magnetic particle complexes;
    flowing the mixture from the vessel into the fluidic device and through a channel in the fluidic device such that said complexes are held in place by the magnet; and
    separating antibody-bound pathogen being held by the magnet from other components in the sample.

2. The method of claim 1, further comprising the step of characterizing the pathogen.

3. The method of claim 2, wherein said characterizing step comprises identifying the pathogen.

4. The method of claim 3, wherein said identifying step is selected from sequencing nucleic acid derived from the pathogen and amplifying the nucleic acid.

5. The method of claim 1, wherein the sample is a blood sample.

6. The method of claim 1, wherein the particles are differentially labeled.

7. The method of claim 6, wherein the particles comprise is an optical label.

8. The method of claim 7, wherein the optical label is a fluorescent label.

9. The method of claim 1, wherein the target-specific binding moieties comprise antibodies.

10. The method of claim 1, wherein the antibodies are monoclonal antibodies.

11. The method of claim 1, wherein the antibodies are polyclonal antibodies.

12. The method of claim 1, wherein the pathogen is gram positive bacteria.

13. The method of claim 1, wherein the pathogen is gram negative bacteria.

14. The method of claim 1, wherein the pathogen is a virus.

15. The method of claim 1, wherein the magnetic particles comprise a plurality of sets, wherein members of different sets are conjugated to different antibodies that are specific for different pathogen.

16. The method of claim 15, wherein the different sets are provided at different concentrations.

17. The method of claim 15, wherein the different sets are provided at the same concentrations.

18. The method of claim 1, wherein the magnetic particles are beads.

19. The method of claim 18, wherein the bead are from about 100 nm to about 250 nm in diameter.

* * * * *